United States Patent [19]

Denis et al.

[11] Patent Number: 5,770,768
[45] Date of Patent: Jun. 23, 1998

[54] METHOD FOR PREPARING CARBOXYLIC ACIDS BY CARBONYLATION IN THE PRESENCE OF IRIDIUM

[75] Inventors: Philippe Denis, Decines; Robert Perron, Charly; Joël Schwartz, Caluire, all of France

[73] Assignee: Acetex Chimie, Paris, France

[21] Appl. No.: 817,701

[22] PCT Filed: Nov. 3, 1995

[86] PCT No.: PCT/FR95/01446

§ 371 Date: Jun. 3, 1997

§ 102(e) Date: Jun. 3, 1997

[87] PCT Pub. No.: WO96/14286

PCT Pub. Date: May 17, 1996

[30] Foreign Application Priority Data

Nov. 4, 1994 [FR] France ................................. 94 13175

[51] Int. Cl.⁶ .................................................. C07C 51/12
[52] U.S. Cl. ......................................................... 562/519
[58] Field of Search ............................................. 562/519

[56] References Cited

U.S. PATENT DOCUMENTS 3,772,380  11/1973  Paulik et al. ............................ 560/232
4,381,221  4/1983  Isshiki et al. ............................... 203/6
5,237,097  8/1993  Smith et al. ............................. 562/519

FOREIGN PATENT DOCUMENTS 0 441 260  8/1991  European Pat. Off. .

*Primary Examiner*—Gary Geist
*Assistant Examiner*—Rosalynd Keys
*Attorney, Agent, or Firm*—Dennison, Meserole, Pollack & Scheiner

[57] ABSTRACT

A method for preparing carboxylic acids by carbonylating a reagent, particularly an alcohol, in the presence of an iridium catalyst. According to the method, the liquid phase reaction is carried out in a first zone in the presence of an iridium catalyst, and the resulting reaction mixture is partially vaporised in a second zone. The vaporised fraction containing the carboxylic acid is later purified and the unvaporised liquid fraction containing the catalyst is recirculated to the first zone. The method is characterised in that said unvaporised fraction is contacted with carbon monoxide in such a way that this compound is not returned to the second zone.

12 Claims, 3 Drawing Sheets

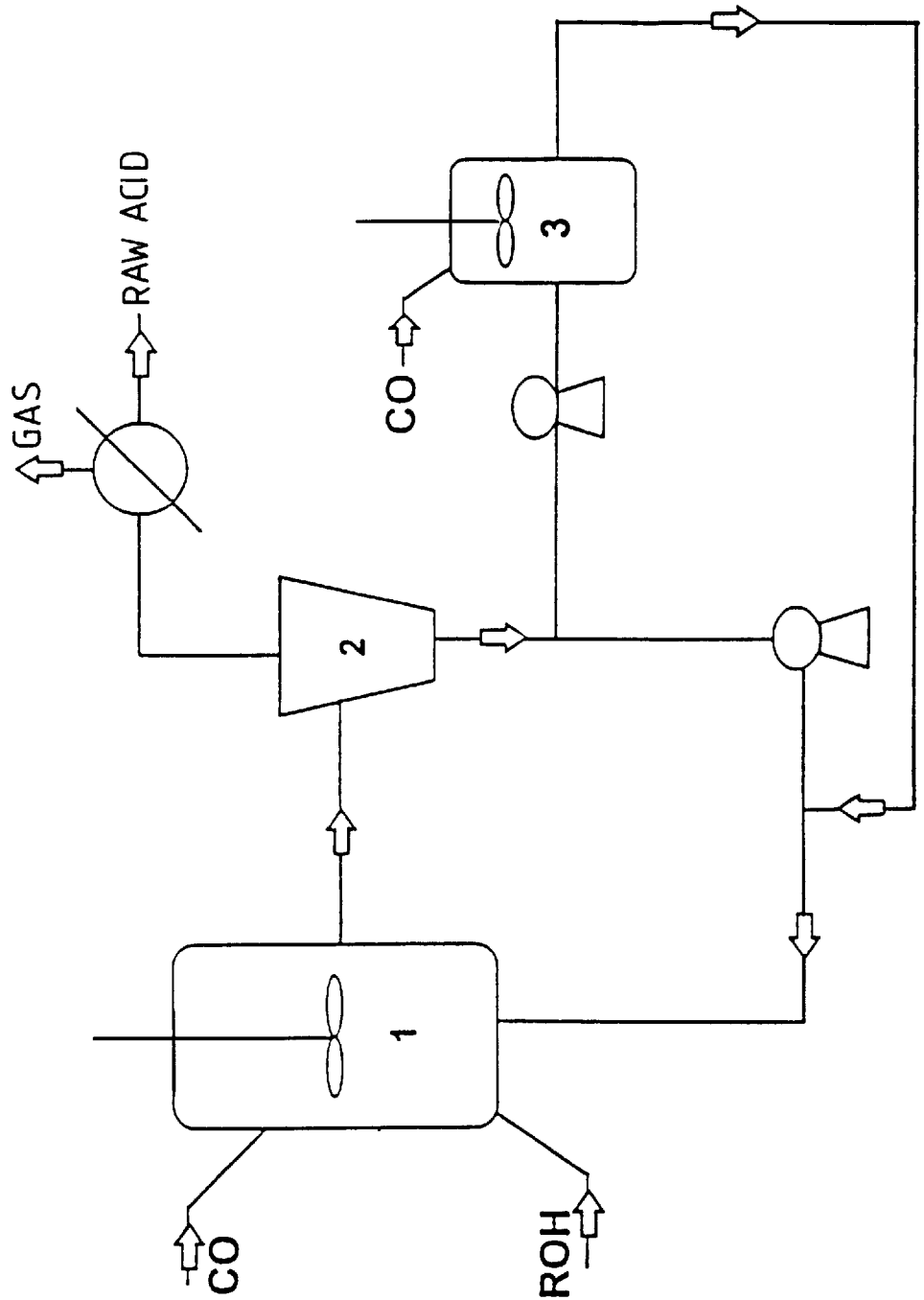

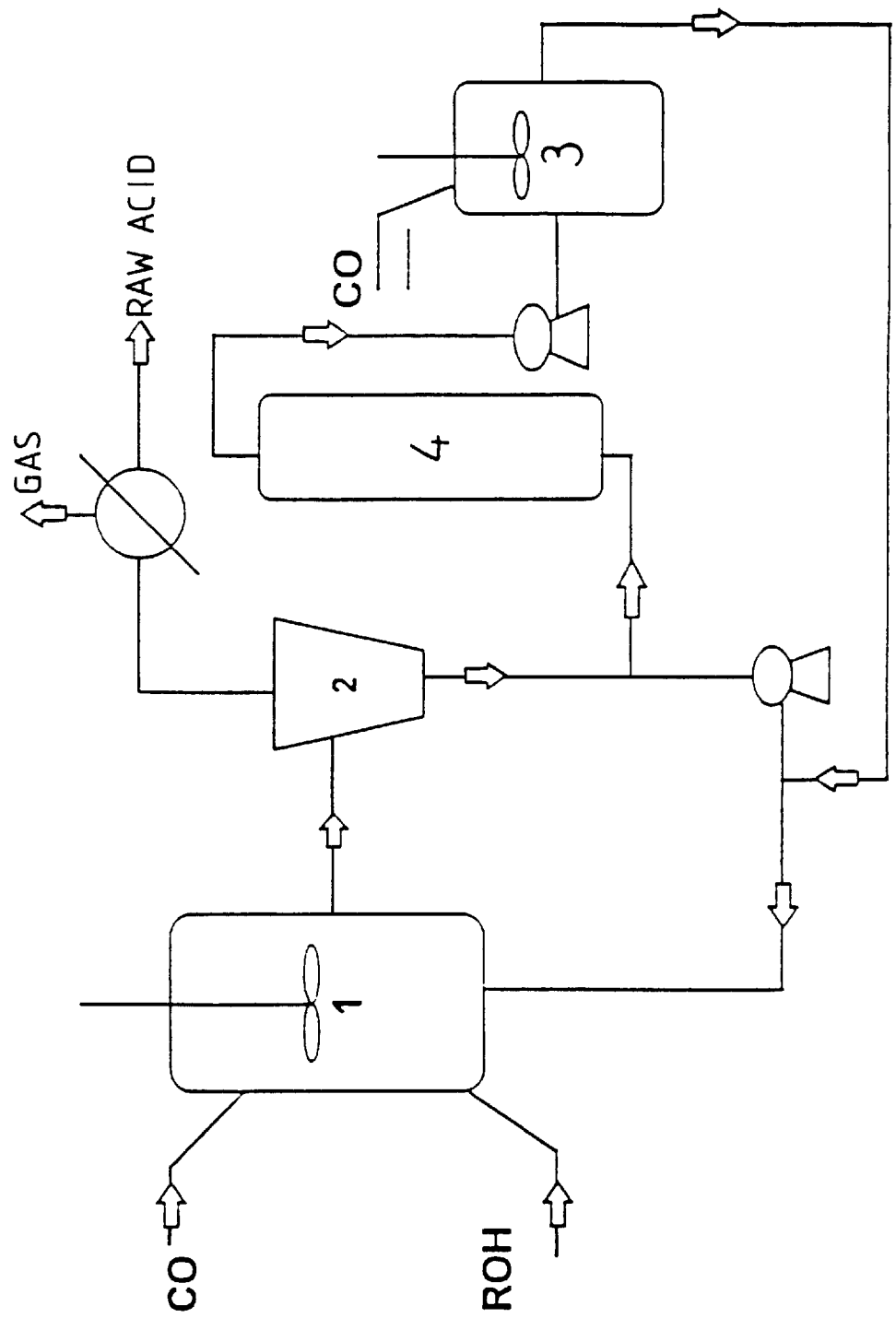

METHOD FOR PREPARING CARBOXYLIC ACIDS BY CARBONYLATION IN THE PRESENCE OF IRIDIUM

BACKGROUND OF THE INVENTION

The object of the present invention is a method for preparing carboxylic acids by carbonylation of a reagent, notably selected from the alcohols, in the presence of an iridium-based catalyst.

The carbonylation methods which use soluble iridium-based catalysts for the preparation of carboxylic acids are known methods. Generally, they are carried out in installations which essentially comprise three zones. The first corresponds to the actual reaction zone which comprises a reactor under pressure in which the carbonylation is effected. The second is constituted of a zone for separating the acid formed. This operation is carried out by partial vaporisation of the reaction mixture in an apparatus (called <<flash>>) wherein the pressure is maintained below that in the reactor. The vaporised part is then sent into a third zone wherein the carboxylic acid produced is purified. This zone comprises various distillation columns in which the carboxylic acid produced is separated from water, reagents, and by-products. The part of the mixture which has remained in liquid form upon leaving the vaporisation zone, and which notably comprises the catalyst, is recycled to the reactor. This is classically carried out by means of a pump.

During the implementation of these methods, a decrease in the activity of the catalyst was noticed after passing the unvaporised fraction comprising the catalyst several times in the recycling loop of the flash to the reactor.

SUMMARY OF THE INVENTION

Therefore, the object of the present invention is a method for preparing carboxylic acids by carbonylation in the presence of an iridium-based catalyst, in which method the catalyst is reactivated in a simple and efficient way.

Thus, the method for preparing carboxylic acids according to the invention consists in carrying out the reaction, in the presence of an iridium-based catalyst, in liquid phase in a first zone, then in partially vaporising the reaction mixture obtained in a second zone; the vaporised fraction, which contains the carboxylic acid produced, is subsequently purified and the unvaporised liquid fraction which contains the catalyst is recycled to the first zone. The characteristic of the method is that the unvaporised liquid fraction resulting from the second zone is placed in contact with carbon monoxide in such a way that said compound does not return to the second zone.

BRIEF DESCRIPTION OF THE DRAWINGS

Other advantages and characteristics shall appear more clearly upon reading the following description and drawings, for which:

FIG. 2 represents a second embodiment in which carbon monoxide is dissolved in a part of the unvaporised liquid fraction resulting from the flash.

FIG. 3 represents a variant of the preceding embodiment in which carbon monoxide is dissolved in a part of the unvaporised liquid fraction resulting from the flash, which has been treated beforehand on an ion exchange resin.

DETAILED DESCRIPTION OF THE INVENTION

Figure 1:
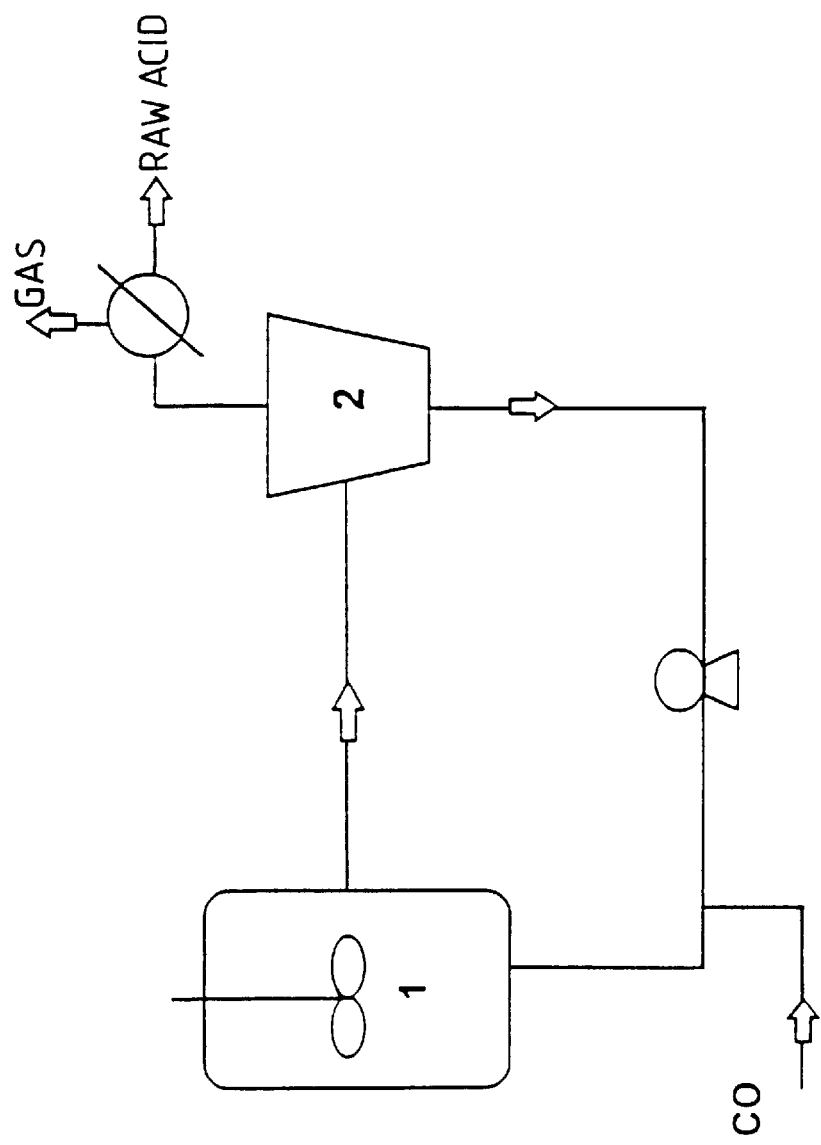
FIG. 1 represents a first embodiment in which the unvaporised fraction is placed in contact with gaseous carbon monoxide.

The method according to the invention enables preventing any loss of carbon monoxide, which is one of the reagents of the carbonylation. In fact, if this gas had been introduced for example into the actual flash zone, there would have been an inevitable loss of said compound. First of all, in order to obtain an effective amount of carbon monoxide so as to reactivate the catalyst, it is necessary to carry out industrially very significant outputs of said gas, even though the partial carbon monoxide pressure maintained is relatively low. Now, the implementation of significant outputs may have consequences on the installation itself, e. g. concerning the size of the fittings. Moreover, the dissolution of carbon monoxide can only be done correctly in the presence of strong stirring. Now a flash does not comprise such means. Thus, the major part of the flow of carbon monoxide under these conditions cannot be conserved in the flash, or a relatively low total pressure is furthermore established. Consequently, the gas escapes with the vaporised fraction of the reaction medium. Now if means of separating the carbon monoxide from the gases produced by the reaction, such as carbon dioxide, methane, or even hydrogen, are not at one's disposal for finally recycling the carbon monoxide, said gas is destroyed. It is also necessary either to loose non-negligible amounts of carbon monoxide, or to foresee an additional investment for the recovery of the latter.

The method according to the invention therefore enables reactivating the catalyst without there being a loss of carbon monoxide and without an additional significant investment being necessary.

The method according to the invention is carried out within the context of the preparation of carboxylic acids by carbonylation.

In the following, contents are expressed in percentages by weight unless otherwise indicated.

The reagent employed in this type of reaction is generally selected from the alcohols. Saturated mono- or di-hydroxylated alcohols having one to ten carbon atoms may be cited amongst the alcohols which may by used. Methanol, ethanol, propanol, butanol, 1,4-butanediol may notably be mentioned as examples of such compounds. The monohydroxylated alcohols are preferred.

It is important to note that the alcohol may be present in the reaction medium as such or in a masked form. It may in fact be in the form of a halogenated derivative and/or an ether and/or an ester obtained by reaction of said alcohol and the carboxylic acid present.

The reaction is carried out in the presence of a catalytic system which comprises on the one hand a soluble iridium species and on the other a halogenated promoter.

Generally, the iridium-based compounds used are selected from the co-ordination complexes of said metal which are soluble in the medium under the reaction conditions. More particularly, co-ordination complexes are used whose ligands are on the one hand carbon monoxide and on the other a halogen, which is particularly iodine. Of course, it is possible to use soluble organic ligand-based complexes. As convenient iridium-based compounds the U.S. Pat. No. 3,772,380 may be referred to which gives an indicative list thereof.

Regarding the promoter, this more particularly corresponds to the halogenated form of the above-mentioned alcohol. Preferably, the halogen is iodine.

The halogenated promoter content is generally below 10%.

Furthermore, the carbonylation is carried out in the presence of the ester which corresponds to the alcohol and the acid produced.

More particularly, the ester content is between 2 and 40%.

The carbonylation is further carried out in the presence of water. The water content may vary within large limits. It is, however, preferably below 10%.

The reaction mixture may optionally comprise a compound selected from the soluble iodides which can be introduced into the reaction medium as such or even in the form of compounds which can form soluble iodides.

Thus, the iodides introduced into said mixture as such are selected from the inorganic iodides, notably such as the alkaline earth metal iodides or alkali metal iodides which have at least one organo-phosphorus group and/or at least one organo-nitrogen group which reacts with iodine-based compounds present in the reaction medium giving ionic species which contain this halogen.

Potassium iodide, lithium iodide and sodium iodide may be cited as preferred inorganic iodides, and methyltriphenylphosphonium iodide and N-methyltriethylammonium iodide may be cited as organic iodides.

Alkali metal or alkaline earth metal carboxylates such as notably lithium acetate are particularly convenient as iodide precursors.

The amount of iodides present in the medium is such that the iodides introduced/iridium atomic ratio (expressed in mole/mole) be between 0 (excluded) and 10, and more particularly between 0 (excluded) and 3.

Finally, the reaction solvent is advantageously the carboxylic acid which is desired to produce.

The carbonylation reaction is carried out at a temperature between 150° and 250° C.

The total pressure in the reactor is usually between 1 and 100 absolute bars.

The partial carbon monoxide pressure in the reactor varies more particularly between 1 and 50 absolute bars.

The carbon monoxide may be introduced in the reactor pure or diluted in a gas such as hydrogen, methane, or even nitrogen.

The reaction mixture is then treated continuously in the zone for separating the acid formed in which a fraction of said reaction mixture is vaporised. In this part, the total pressure is lower than that of the reactor. It is generally between 1 and 20 absolute bars.

The operation may take place without the contribution of heat to the flash (adiabatic conditions) or even with the contribution of heat. According to a preferred variant, the partial vaporisation is effected in an adiabatic flash.

As has been mentioned beforehand, the vaporised fraction comprises the carboxylic acid production but also the reagents and by-products of the reaction. This vaporised fraction is sent into the acid purification zone which classically comprises several distillation columns in which the produced acid is purified.

The unvaporised liquid fraction which notably contains the catalyst is recovered at the foot of the flash in order to be recycled in the reactor.

The carbonylation method according to the invention therefore consists in placing said unvaporised fraction in contact with carbon monoxide in such a way that this compound does not return into the second zone, i. e. that of the partial vaporisation of the reaction mixture. The saying << the introduction of carbon monoxide is such that said compound does not return to the second zone>> means using the means which prevent the degassing of this compound directly towards the flash.

Without being limited by any one theory, it has been found that the catalyst had a tendency to form inactive species according to a relatively slow and reversible process. These species cause a lowering of the activity of the catalyst after passing several times in the recycling loop of the separation zone to that of reaction. Now the introduction of carbon monoxide into this part of the method enables reducing the concentration of these inactive species in an unexpected way and consequently enables regaining a significant level of activity.

According to a first variant of the invention, the carbon monoxide is introduced in the form of a gas.

In order not to have a return of said compound towards the flash, the introduction takes place downstream from the pump by which the unvaporised liquid fraction is recycled to the reactor.

The carbon monoxide may be employed pure or may even comprise other gases such as hydrogen, methane, or nitrogen. Preferably, the carbon monoxide used is sufficiently pure so as to prevent the accumulation of too many gases which are not active for the carbonylation reaction.

The partial pressure of gas introduced, which comprises a major part of carbon monoxide, varies within large limits. It is more particularly between 1 and 100 absolute bars.

The unvaporised fraction may furthermore undergo any type of treatment, notably with the aim of purifying it, such as for example a treatment for removing the corrosive metals, which shall be detailed further on.

According to a second variant of the present method, the unvaporised fraction of the reaction mixture resulting from the flash is placed in contact with a liquid flow which contains dissolved carbon monoxide, before being returned to the reactor.

This variant is advantageous in the sense that introducing a liquid in which carbon monoxide is dissolved enables rendering this compound instantaneously active.

The carbon monoxide may here again be employed pure or may even comprise other gases such as hydrogen, methane, or nitrogen. What has been indicated on this subject in the first variant remains valid here.

The amount of carbon monoxide introduced is at the most equal to the solubility limit of this gas in the liquid employed, according to the conditions of temperature and pressure. More particularly, the amount of carbon monoxide dissolved is between 0 (excluded) and 10%, this content being linked to the temperature and the pressure of the liquid.

The liquid flow in which the carbon monoxide is selected such that it is compatible with the carbonylation reaction mixture.

According to a first embodiment of the invention, the liquid flow in which the carbon monoxide is dissolved is constituted of carboxylic acid and/or any other reagent employed during the carbonylation. The carboxylic acid, or any other reagent, may be used pure or, advantageously, may even originate from the purification zone situated downstream.

According to a second embodiment of the invention, the carbon monoxide is dissolved in a solution which further comprises the catalyst. According to this embodiment, at least one part of the unvaporised fraction originating from the separation zone is derived from the recycling loop in order to be placed in contact with the carbon monoxide. The liquid flow thus treated is then combined with the other part of the liquid fraction which leaves the flash.

This embodiment is particularly advantageous in the sense that a part of the catalyst is treated with carbon monoxide, thus enabling its reactivation.

According to a particular variant of this second embodiment, the part of the liquid fraction in which the carbon monoxide is dissolved is treated beforehand on an ion exchange resin in order to remove the corrosive metals. This is carried out by any means known to the person skilled in the art.

Thus, resins of the strong acid type may more particularly be used, in a hydrogen form. These resins may be in the form of a gel or even in micro-crosslinked form.

The placing in contact is carried out on a fixed bed or on a fluidised bed.

The temperature at which the treatment is carried out must of course be adapted to the resistance of the resin. Generally, it is between room temperature and 100° C.

Whatever the solution in which the carbon monoxide is dissolved, the dissolution operation of the gas takes place in an apparatus with strong stirring.

Any means may be used for obtaining such a result, whether it be of mechanical nature or not.

The temperature of placing in contact is between 25° and 200° C.

The pressure is at least equal to the pressure held in the reactor. More particularly, the pressure is between 1 and 100 absolute bars.

Preferably, the solution comprising the dissolved carbon monoxide is introduced into the part of the recycling loop in such a way as to prevent the degassing of the carbon monoxide and its driving off towards the flash, as well as to prevent the cavitation of the pump with which the liquid fraction originating from the flash is returned to the reactor. The person skilled in the art with his or her own knowledge of chemical engineering has even to determine the appropriate place for the introduction of the solution which contains the dissolved carbon monoxide.

It is to be borne in mind that the degassing of a part of the carbon monoxide towards the reactor does not present any particular problem since this compound is consumed in the carbonylation reaction and is therefore not lost with the gaseous by-products.

It is to be noted that the context of the present invention shall not be left by using a combination of both variants described above, i. e. the placing the unvaporised fraction in contact with the carbon monoxide dissolved or not in the liquid flow.

DESCRIPTION OF THE PREFERRED EMBODIMENTS

FIG. 1 describes an embodiment of the first variant, in which the unvaporised fraction is placed in contact with gaseous carbon monoxide. Thus, the carbon monoxide and the alcohol are introduced into the reactor (1) which contains the catalytic system, the ester, the water and the stabiliser. Upon leaving the reactor, the reaction mixture is expanded by means of a valve (which is not shown in the scheme) which causes a partial vaporisation of the mixture and introduced into the flash (2). The vaporised fraction is condensed so as to separate the carboxylic acid to be purified from the non-condensable products which are carbon monoxide, and the gaseous by-products of the reaction. The fraction which remains liquid is itself engaged in the recycling loop towards the reactor. The carbon monoxide is introduced downstream from the pump employed for recycling the liquid fraction.

FIG. 2 describes an embodiment of the second variant in which a part of the unvaporised fraction is placed in contact with carbon monoxide dissolved in a liquid flow. Thus, the carbonylation reaction takes place as represented in the preceding Figure. Upon leaving the reactor, the reaction medium is introduced into the flash (2). The vaporised fraction is condensed in order to separate the carboxylic acid to be purified from the non-condensable products. The fraction which remains liquid is engaged in the recycling loop towards the reactor. A part of this flow is then derived from the recycling loop in order to be introduced into a reactor (3) equipped with means of stirring and carbon monoxide introduction. Once the dissolution of this gas has taken place, the liquid enriched in carbon monoxide is combined with the flow which has not been treated, after having been beforehand and if need be expanded so as to regain a pressure similar to that of the reactor, by means of a valve which is not shown.

FIG. 3 represents a variant of the embodiment described in the preceding Figure. The difference between these two embodiments is in the fact that the fraction derived from the recycling loop is treated by passing it in a column (4) on an ion exchange resin before placing it in contact with the carbon monoxide.

On both of the last two Figures, the derivation of the flow to be placed in contact with the carbon monoxide is carried out upstream from the pump which enables the recycling of the liquid towards the reactor. The context of the present invention would not be left in carrying out this derivation downstream from this same pump.

Similarly, for the same two figures, the point of contact between the liquid comprising the dissolved carbon monoxide and that which has not been treated with this gas is situated downstream from the above-mentioned pump. Here again, the context of the present invention would not be left in carrying this out upstream from the pump.

Of course, these three figures are only examples of the implementation of the invention and must not be considered as being limitations of it.

What is claimed is:

1. Method for preparing a carboxylic acid by carbonylation of an alcohol or a reactive compound thereof, comprising reacting the alcohol or reactive compound thereof with carbon monoxide in the presence of an iridium-based catalyst, in a liquid phase reaction medium in a first zone, to produce a reaction mixture which is partially vaporized in a second zone to produce a vaporized fraction containing the carboxylic acid which is subsequently purified and an unvaporized liquid fraction containing the catalyst, and recycling the unvaporized liquid fraction to the first zone, wherein said unvaporized liquid fraction being recycled is placed in contact with carbon monoxide in such a way that carbon monoxide does not return towards the second zone.

2. Method according to claim 1, wherein the unvaporized fraction is recycled by means of a pump and carbon monoxide is introduced downstream from said pump.

3. Method according to claim 1, wherein the unvaporized fraction is placed in contact with carbon monoxide dissolved in a liquid flow.

4. Method according to claim 3, wherein the liquid flow in which the carbon monoxide is dissolved is a solution compatible with the reaction mixture.

5. Method according to claim 3, wherein the liquid flow in which the carbon monoxide is dissolved contains the catalyst.

6. Method according to claim 5, wherein the liquid flow is a part of the unvaporized fraction.

7. Method according to claim 6, wherein said unvaporized fraction is treated on an ion exchange resin before said placing in contact.

8. Method according to any one of claim 3, wherein the dissolved carbon monoxide is from 0 (excluded) to 10%, according to the conditions of temperature and pressure of the liquid.

9. Method according to claim 1, wherein the alcohol is a mono- or di-hydroxy alcohol having one to ten carbon atoms.

10. Method according to claim 9, wherein the alcohol is selected from the group consisting of methanol, ethanol, propanol, butanol and 1,4-butandiol.

11. Method according to claim 1, wherein the alcohol is present in the reaction medium in a masked form.

12. Method according to claim 11, wherein the alcohol is present in the form of a halogenated alcohol, an ether, an ester or a mixture thereof.

* * * * *